US00PP28560P2

(12) United States Plant Patent
Apps

(10) Patent No.: US PP28,560 P2
(45) Date of Patent: Oct. 24, 2017

(54) DAYLILY PLANT NAMED 'BLAZING RETURNS'

(50) Latin Name: ***Hemerocallis hybrida*/Daylily**
Varietal Denomination: cv. Blazing Returns

(71) Applicant: BlewLine Nursery, Inc., Bridgeton, NJ (US)

(72) Inventor: Darrel A. Apps, Wild Rose, WI (US)

(73) Assignee: BLEWLINE NURSERY, INC., Bridgeton, NJ (US)

( * ) Notice: Subject to any disclaimer, the term of this patent is extended or adjusted under 35 U.S.C. 154(b) by 0 days.

(21) Appl. No.: 14/999,856

(22) Filed: Jul. 12, 2016

(51) Int. Cl.
*A01H 5/02* (2006.01)

(52) U.S. Cl.
USPC ..... Plt./312

(58) Field of Classification Search
USPC ..... Plt./312
See application file for complete search history.

*Primary Examiner* — Annette Para
(74) *Attorney, Agent, or Firm* — Buchanan Ingersoll & Rooney PC

(57) ABSTRACT

A new and distinct *Hemerocallis* cultivar of the semi-evergreen type is provided. The new cultivar is very floriferous and forms attractive ruffled red flowers displaying substantial substance, and a tunnel-shaped form over an extended period of time. In U.S.D.A. Hardiness Zone No. 6, blooming commonly begins during late June and commonly ends in mid-September. The new cultivar displays a plurality of fans and a plurality of scapes per fan. In excess of 15 buds commonly are formed per scape. The new cultivar is well suited for growing as distinctive colorful ornamentation in the landscape.

1 Drawing Sheet

Botanical/commercial classification: *Hemerocallis hybrida*/Daylily.

Varietal denomination: cv. Blazing Returns.

SUMMARY OF THE INVENTION

The present invention comprises a new and distinct cultivar of *Hemerocallis* plant of the semi-evergreen type, and hereinafter is referred to by the cultivar name 'Blazing Returns'.

The new cultivar is the product of a planned breeding program which had as its objective the creation of a new Daylily cultivar that is intended for use as attractive ornamentation in the landscape.

The cross that resulted in the production of the new cultivar of the present invention was carried out in a controlled environment during May, 2003, at Bridgeton, N.J., U.S.A. The female parent (i.e., the seed parent) of the new cultivar was the 'Endless Heart' cultivar, which displays a bright crimson red flower. Such female parent is registered with the American *Hemerocallis* Society and was granted U.S. Plant Pat. No. 16,515 P2. The male parent (i.e., the pollen parent) of the new cultivar was the 'Regency Dandy' cultivar (non-patented in the United States), which displays a medium red flower. Such male parent is registered with the American *Hemerocallis* Society.

The parentage of the new cultivar of the present invention can be summarized as follows:

'Endless Heart'×'Regency Dandy'.

The seeds resulting from the above pollination were sown and small plantlets were obtained which were physically and biologically different from each other. A number of such plants were transplanted into the field at Bridgeton, N.J., U.S.A., during June, 2004. Selective study during May-June 2005 resulted in the identification of a single plant of the new cultivar.

It was found that the new *Hemerocallis* plant of the present invention is of the semi-evergreen type:

(a) forms attractive ruffled red flowers, having a substantial substance and funnel form,
(b) possesses a long blooming season with substantially multiple repeat blooming,
(c) exhibits a propensity to readily display a plurality of fans,
(d) readily forms a plurality of scapes per fan over the flowering season, and
(e) commonly produces in excess of 15 buds on each scape.

When compared to the 'Endless Heart' cultivar, the 'Blazing Returns' cultivar has a stronger and better-branched scape and flowers with a more intense shade of deep red coloration. When compared to the 'Regency Dandy' cultivar, the 'Blazing Returns' cultivar has a flowers with a ruffled petal edge, more structured petal shape, and a more uniform red coloration.

The 'Blazing Returns' cultivar resembles some well-known cultivars, such as the 'Stella D' Oro' cultivar (non-patented in the United States) and the 'Happy Returns' cultivar (non-patented in the United States) in the sense that it commonly possesses an unusually long and substantially continuous blooming season (i.e., a multiple repeat character) of up to approximately 75 days in U.S.D.A. Hardiness Zone No. 6. Such blooming commonly begins during late June and commonly ends in mid-September. This compares to a bloom period of less than about 30 days for over 99 percent of the hybrid Daylilies that presently are available in the trade.

As indicated, the 'Blazing Returns' plant exhibits attractive ruffled red flowers. Such flowers can be readily distinguished from the orange-yellow flowers of the 'Stella D' Oro' cultivar, and the medium yellow flowers of the 'Happy Returns' cultivar. To the best knowledge of the originator, the 'Blazing Returns' cultivar is the first long and substantially continuously blooming Daylily having flowers that exhibit such a red hue combined with substantial flower substance on a substantial scape.

The new cultivar can form up to 4 or more fans per year. This compares to approximately 6 to 8 fans per year for the 'Stella D' Oro' cultivar and the 'Happy Returns' cultivar. Most Daylily cultivars form only approximately 2 to 3 fans per year. Also, the new cultivar commonly forms several scapes per fan during the flowering season, unlike most Daylilies that commonly produce only one scape per fan.

Asexual reproduction of the new cultivar by division was initially carried out on Sep. 1, 2005, at Bridgeton, N.J., U.S.A. At the time of such asexual reproduction, the original plant of the new cultivar consisted of a clump of four fans that were phenotypically identical to each other. More specifically, the clump of the new cultivar was removed from the field and the fans were divided. It has been demonstrated that the characteristics of the new cultivar are firmly fixed and are well retained following this asexual reproduction.

The 'Blazing Returns' plant has not been observed under all possible environmental conditions to date. Accordingly, it is possible that the phenotype may vary somewhat with variations in the environment, such as temperature, light, day length, contact with pesticides, etc.

The new 'Blazing Returns' cultivar will be marketed by the Assignee under the HAPPY EVER APPSTER trademark beginning in June 2016.

BRIEF DESCRIPTION OF THE PHOTOGRAPHS

The accompanying photographs show the original plant of the new cultivar in color as nearly true as it is possible to make the same in color illustrations of this character. Each photograph was prepared on Jun. 26, 2015, while the plant was being grown outdoors in a field at Bridgeton, N.J., U.S.A. The attractive ruffled red flowers are illustrated as well as foliage, and reproductive parts.

DETAILED BOTANICAL DESCRIPTION

Figure 1:
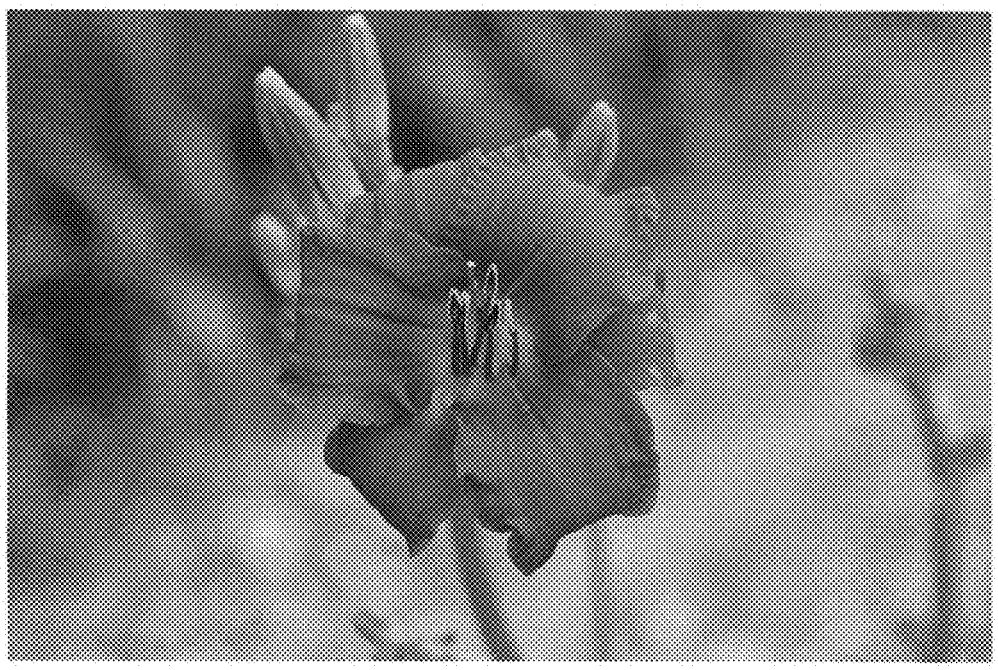
FIG. 1 illustrates a close view of a red opened flower.
Figure 2:
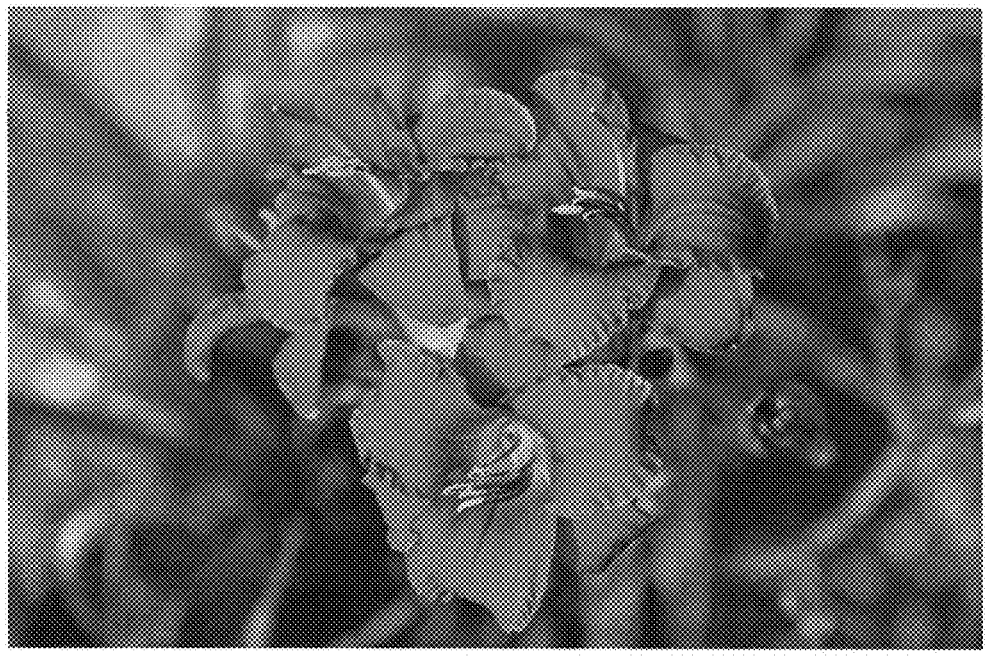
FIG. 2 illustrates a cluster of red opened flowers.

The chart used in the identification of the colors described herein is The R.H.S. Colour Chart of The Royal Horticultural Society, London, England (1995 Edition). The original plant of the new cultivar is described, except as otherwise indicated, when observed and described during June 2016 while growing at Bridgeton, N.J., U.S.A., under field growing conditions.

Classification:

*Botanical.*—*Hemerocallis hybrida.*

*Commercial name.*—Daylily.

*Cultivar.*—Blazing Returns.

Plant:

*Height.*—Approximately 35 cm at an age of one year.

*Width.*—Approximately 53 cm at an age of one year.

*Foliage.*—Form: single stem, substantially erect fan-shaped plant having narrow arching, long, keeled, grass-like glabrous to slightly textured leaves that are two-ranked at the base of the scape. Quantity: abundant, with a mature plant commonly having approximately 16 leaves per fan. Leaf Size: commonly approximately 2 cm in width on average, and approximately 48 cm in length on average. Leaf Shape: sessile, linear and long-keeled with entire margins, and a sharply acuminate apex. Texture: glabrous. Color: On the upper surface, near Yellow-Green Group 146A in color, and on the under surface, near Green Group 137B in color. Leaf Venation: On the upper surface, faint venation of near Green Group N137A, and on the under surface venation near Green Group N137A and strongly keeled at the mid-rib. Type: semi-evergreen with the plant commonly retaining some green coloration during the winter in U.S.D.A. Hardiness Zone No. 6b.

*Scape.*—Color: near Yellow-Green Group 146A. Length: commonly approximately 51 cm on average. Width: commonly approximately 7 mm on average.

*Disease resistance.*—Typical of *Hemerocallis* with no problems having been observed to date.

Inflorescence:

*Bud.*—Form: modified oblanceolate slightly tapered cylindrical shape. Apex: rounded upper quarter that comes to a point. Size: on the day prior to opening commonly approximately 5.5 cm in length on average, and approximately 2 cm in width on average. Number: commonly in excess of 15 per scape. Color: near Greyed-Orange Group 172A. Opening Rate: commonly approximately three hours on average.

*Peduncle.*—Length: commonly approximately 15 mm on average. Width: commonly approximately 7 mm on average. Strength: tends to be rigid and sturdy. Color: near Yellow-Green Group 146B.

*Flower.*—Size: commonly has a diameter of approximately 9 cm on average and a depth of approximately 5 cm on average. Borne: singly on the branchlets of a sturdy erect rachis which is ramulose. Each scape commonly has at least 15 peduncles, each of which commonly divides into approximately 2 pedicels. Blooms Per Scape: commonly approximately 1 or 2 each day. Tepalage: each flower consists of six perianth segments wherein there are three outer tepals (sepals) and three inner tepals (petals) all in an imbricated arrangement. Sepal Shape: oblanceolate with slightly undulated entire margins and an acuminate apex. Sepal Texture: slightly ribbed. Sepal Size: commonly approximately 7 cm in length on average, and approximately 2.5 cm in width on average. Sepal Color: the outer surface is near Orange-Red N34B changing to Yellow-Green Group 151B at the base, and the inner surface is near Greyed-Purple 185A changing to near Yellow-Green Group 151A at the base. Petal Texture: with a ruffled edge. Petal Size: commonly approximately 7 cm in length on average, and approximately 4 cm in width on average. Petal Color: the outer surface is near Orange-Red Group N34A changing to near Yellow-Green Group 151B at the base, and the inner surface is near Greyed-Purple Group 185A changing to near Yellow-Green Group 151B at the base. Eyezone: none. Blooming Habit: the flowers commonly bloom substantially continuously and the scape commonly is substantially continuously in bloom for up to approximately 75 days per year in Hardiness Zone No. 6. Effects of Weather: the flowers will withstand rain damage in view of the strength of the tepals. Lasting Quality: commonly at least 16 hours. As with other *Hemerocallis* cultivars known to the inventor, the flower color eventually fades somewhat during the day with the natural effects of environmental conditions and ongoing maturity. Fragrance: none.

*Reproductive organs*.—Stamen Number: six per flower. Stamen Disposition: individually inserted at the summit of the perianth tube. Anther Disposition: introrse. Anther Size: approximately 8 mm in length. Anther Color: near Brown Group 200A. Filament Configuration: slender. Filament Length: commonly approximately 4 cm on average. Filament Color: near Yellow-Green Group 151A becoming near Red-Purple Group 59A at the end. Pollen Color: near Yellow-Orange Group 23A. Pistil Number: one per flower. Style Length: approximately 6 cm on average. Style Color: near Greyed-Yellow Group 162A becoming near Red-Purple Group 59B at the end. Stigma Color: near Yellow-Green Group 151D. Ovaries: three-celled, oblong, becoming a loculiedally three-valved capsule, and near Yellow-Green Group 150B in coloration.

*Fruit*.—Configuration: the seed pod is in the form of an ovoid capsule. Color: at maturity commonly is near Yellow-Green Group 146A. Fertility: the seeds are fertile.

Hardiness: Cold tolerance is displayed in U.S.D.A. Hardiness Zone No. 5a, and heat tolerance is displayed in U.S.D.A. Hardiness Zone No. 8b.

I claim:

1. A new and distinct cultivar of *Hemerocallis* plant of the semi-evergreen type, which:

(a) forms attractive ruffled red flowers having substantial substance, and a funnel-shaped form, (b) possesses a long blooming season with substantially continuous blooming, (c) exhibits a propensity to readily display a plurality of fans, (d) readily forms a plurality of scapes per fan over the flowering season, and (e) produces a plurality of buds on each scape;

substantially as illustrated and described.

* * * * *